(12) United States Patent
Fehr et al.

(10) Patent No.: US 9,827,341 B2
(45) Date of Patent: Nov. 28, 2017

(54) METHOD FOR STERILISING AND STERILISING DEVICE

(75) Inventors: Thorsten Fehr, Losheim am See (DE); Claus Haupert, Nalbach (DE); Franz Kugelmann, St. Wendel/Bliesen (DE); Nicole Simon, Schmelz (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1140 days.

(21) Appl. No.: 13/808,694

(22) PCT Filed: Jul. 5, 2011

(86) PCT No.: PCT/EP2011/003342
§ 371 (c)(1),
(2), (4) Date: Jan. 7, 2013

(87) PCT Pub. No.: WO2012/003967
PCT Pub. Date: Jan. 12, 2012

(65) Prior Publication Data
US 2013/0105025 A1    May 2, 2013

(30) Foreign Application Priority Data

Jul. 5, 2010 (DE) .......................... 10 2010 026 104

(51) Int. Cl.
*A61L 2/18* (2006.01)
*A61L 2/20* (2006.01)
(Continued)

(52) U.S. Cl.
CPC .............. *A61L 2/186* (2013.01); *A61L 2/202* (2013.01); *A61L 2/208* (2013.01); *F16L 11/00* (2013.01);
(Continued)

(58) Field of Classification Search
CPC .................................. A61L 2/186; F16L 11/00
(Continued)

(56) References Cited

U.S. PATENT DOCUMENTS 4,203,943 A    5/1980  Gillis et al.
5,120,512 A *  6/1992  Masuda ................. A61L 2/202
                                                    422/198
(Continued)

FOREIGN PATENT DOCUMENTS

CN    101495248    7/2009
CN    101516321    8/2009
(Continued)

OTHER PUBLICATIONS

S.S. Block "Disinfection, Sterlization, and Preservation Chapter 38." Dec. 31, 2001, pp. 751-753.

*Primary Examiner* — Sean E Conley
(74) *Attorney, Agent, or Firm* — Jacobson Holman, PLLC.

(57) ABSTRACT

The present invention relates to a method for sterilizing at least one object, wherein the object is exposed to a sterilization agent, wherein at least one first support pressure and at least one second support pressure are applied and wherein a sterilization of a first region of the object takes place by the sterilization agent at the first support pressure and a sterilization of a second region of the object takes place at the second support pressure.

Figure 1:
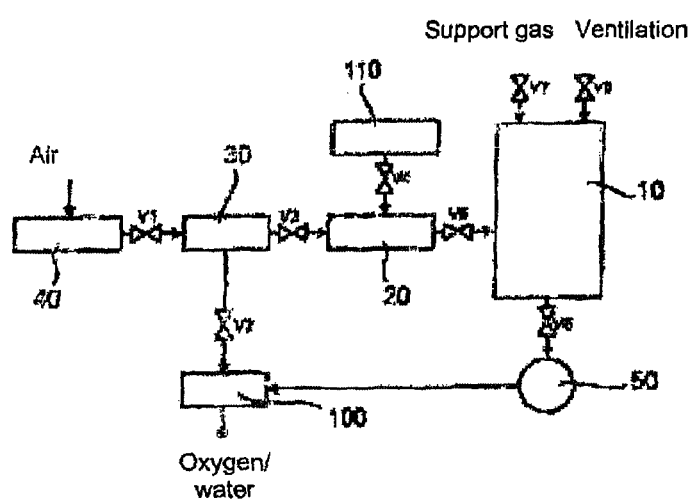

The present invention furthermore relates to a sterilizing apparatus and to a use herefor.

22 Claims, 3 Drawing Sheets

(51) Int. Cl.
*F16L 11/00* (2006.01)
*A61L 2/08* (2006.01)
*A61L 2/10* (2006.01)

(52) U.S. Cl.
CPC .............. *A61L 2/081* (2013.01); *A61L 2/10* (2013.01); *A61L 2202/122* (2013.01); *A61L 2202/14* (2013.01); *A61L 2202/24* (2013.01)

(58) Field of Classification Search
USPC .......................................... 422/33, 105, 295
See application file for complete search history.

(56) References Cited

U.S. PATENT DOCUMENTS

| | | | | |
|---|---|---|---|---|
| 5,527,508 A | * | 6/1996 | Childers | ................ A61L 2/20 422/28 |
| 5,556,607 A | | 9/1996 | Childers et al. | |
| 5,961,921 A | * | 10/1999 | Addy | ..................... A61L 2/14 422/300 |
| 2002/0085950 A1 | | 7/2002 | Robitaille et al. | |
| 2003/0235511 A1 | * | 12/2003 | Jacobs | ................... A61L 2/208 422/28 |
| 2007/0053850 A1 | | 3/2007 | Tichy et al. | |
| 2011/0180114 A1 | | 7/2011 | Butterbaugh et al. | |

FOREIGN PATENT DOCUMENTS

| | | |
|---|---|---|
| EP | 1159971 | 12/2001 |
| EP | 1 175 230 | 1/2002 |
| EP | 1 455 843 | 9/2004 |
| WO | WO 93/17726 | 9/1993 |
| WO | WO 00/66186 | 11/2000 |
| WO | WO 03/039607 | 5/2003 |
| WO | WO 2005/031220 | 4/2005 |

\* cited by examiner

METHOD FOR STERILISING AND STERILISING DEVICE

This is a national stage of PCT/EP11/003342 filed Jul. 5, 2011 and published in German, which has a priority of German no. 10 2010 026 104.1 filed Jul. 5, 2010, hereby incorporated by reference.

The present invention relates to a method and to an apparatus for sterilizing one or more objects.

The sterilization processes used today such as the so-called ETO sterilization, gamma radiation or also steam sterilization are unsuitable for certain sterilization procedures since they in part work with high temperatures and so may damage the object to be sterilized, cause excessive costs and/or are not environmentally friendly. This applies above all to the named ETO sterilization.

It is furthermore known to carry out the sterilization with the aid of ozone. This has the advantage, in particular over ETO sterilization, that e.g. the ozone and $H_2O_2$ can be converted to oxygen and water and thus made harmless via a catalytic converter after sterilization has taken place. Sterilization methods which work under the use of ozone are likewise known from the prior art.

It is thus known from EP 1 175 230 B1 and EP 1 455 843 B1, for example, to carry out a sterilization procedure such that the humidification of the atmosphere located in the sterilization chamber takes place after the evacuation of a sterilization chamber and then the filling with ozone whereby a sterilization procedure is initiated. These treatment steps are repeated before the sterilization chamber is flushed and finally opened so that the sterilized objects can be removed. The apparatus and methods known from the named documents are only suitable in practice for small units such surgical instruments in small containers due to their design and to the conducting of the method.

It is therefore the object of the present invention to further develop a method and an apparatus of the initially named kind in an advantageous manner, in particular such that a sterilization method and an apparatus herefor are provided by means of which a safe and reliable sterilization is also possible of objects which are difficult to sterilize, such as long hose systems and/or hose systems closed at one side.

This object is achieved in accordance with the invention by a method having the features of claim 1. Provision is accordingly made that in a method for sterilizing at least one object, the object is exposed to a sterilization agent, wherein at least one first support pressure and at least one second support pressure are applied and wherein a sterilization of at least one first region of the object takes place by the sterilization agent at the first support pressure and a sterilization of at least one second region of the object takes place at the second support pressure.

The advantage in particular thereby results that an ETO-free, reliable and safe sterilization can be achieved. The support pressure can be generated by the addition of a support gas in a sterilization chamber, whereby the sterilization agent introduced into the sterilization chamber acts on the object to be sterilized and sterilizes it regionally.

It is in particular possible that the object is a disposable of some kind which has regions such as e.g. a lumen or the like which are difficult to access by the sterilization agent due to the geometry of the object.

The object can be a hose system, in particular a medical hose system or a so-called hose kit, for instance for use in hemodialysis. This hose system is preferably sterilized regionally in dependence on this support pressure. Depending on the applied support pressure, the sterilization agent can be transported into the lumen of the hose system.

It is in particular possible to be able to sterilize long hose systems or hose kits even if they are introduced into gas-permeable outer packaging and/or are closed at one side.

It can advantageously thus be prevented that at high pressure values the sterilization agent is concentrated at the center of e.g. hose systems to be sterilized, whereas it is diluted at the respective ends by the support gas. It becomes possible to take the circumstance into account that when a low support pressure is used, the outer ends of the object to be sterilized are rather reached, the hose ends in a hose system, for instance. It now becomes possible by the use of different support pressures to fill all the regions of the object to be sterilized in a targeted manner by the sterilization agent. It is particularly advantageous that the sterilization is also possible in all regions of a closed lumen.

A further advantage is that a safe alternative to so-called gamma sterilization is provided. It can in particular thus be prevented that a change to the material, in the worst case damage to the material, of the object to be sterilized arises as a consequence of the radiation It is furthermore conceivable that the sterilization agent at least partly includes ozone and/or hydrogen peroxide or one or more of the reaction products of these substances. For example, when hydrogen peroxide is used as the sterilization agent, a preheating of the sterilization chamber and of the sterilization product is carried out. On the use of ozone as the sterilization agent, this is not absolutely necessary. It is generally conceivable, for example, only to use hydrogen peroxide or only ozone as the sterilization agent.

It is furthermore possible that the at least one first support pressure and/or the at least one second support pressure is/are generated by introduction of a support gas into a sterilization chamber.

Provision can be made in dependence on the application purpose and on the property of the object to be stabilized that the at least one first support pressure and/or the at least one second support pressure is/are particularly advantageously below atmospheric pressure. Provision can alternatively be made that the at least one first support pressure and/or the at least one second support pressure is/are at or above atmospheric pressure.

It is of advantage if the support gas at least partly includes or is an inert gas and/or air, preferably sterile air.

It is conceivable that in a first step, the object to be sterilized is inserted into a sterilization chamber; in a second step, the sterilization chamber is evacuated; and, in a third step, the sterilization chamber is humidified and sterilization agent is introduced into the sterilization chamber; in a fourth step, the first support pressure is applied; in a fifth step, the first support pressure is maintained for a point in time or for a duration; in a sixth step, steps two to five are repeated once or a multiple of times; and in a seventh step, the at least one second support pressure is applied.

On the increase in pressure, precipitation of the liquid dissolved in the atmosphere takes place. A mist-like atmosphere is hereby created which shows additional effect as an aerosol. It can be generated by fast cooling of a saturated gas or, here, also by a fast increase in the pressure, with the latter variant being a preferred embodiment of the invention.

It is furthermore possible that in the seventh step, steps two to five or two to six are carried out using the second support pressure.

Provision can advantageously further be provided that in at least one further step, one or more further support pressures are applied and that steps two to five or two to six are carried out accordingly using the further support pressures.

It is furthermore conceivable that the humidification of the sterilization chamber takes place in that a liquid, in particular a mixture containing water and hydrogen peroxide, is brought to vaporization by application of a vacuum, in particular by evacuation, and the vaporized liquid is supplied to the sterilization chamber. It is of advantage that this steam created in this manner and containing hydrogen peroxide in any case does not reach a high temperature which could damage the sterilization product. It is namely a comparatively cold steam.

Provision can moreover be made that the first support pressure is at least approximately 500 mbar abs and/or that the second support pressure is at least approximately 50 mbar abs.

It is furthermore possible that a third support pressure is applied, wherein the third support pressure is preferably up to 50 mbar abs and/or corresponds to the gassing pressure without additional introduction of a support gas, wherein the fourth step, that is, the application of the support pressure, is already carried out by step 3, that is, the introduction of the sterilization agent into the sterilization chamber.

In particular, every pressure or support pressure preferably has an upper limit which amounts to around 1100 mbar.

It is further possible that the sterilization agent is introduced into the sterilization chamber in the form of an aerosol.

Provision can be made that the aerosol is formed by steam containing hydrogen peroxide. Provision can be made, for example, that the hydrogen peroxide used as sterilization agent is directed into the sterilization chamber as steam.

It is also conceivable that the aerosol arises by the introduction of ozone into the liquid which contains water and/or hydrogen peroxide. It is, for example, conceivable to conduct ozone gas through a so-called Laskin nozzle. The outlet opening of this nozzle is arranged beneath the level of a liquid which comprises hydrogen peroxide and/or water or which includes one or more of these substances. There are no liquid drops, which have a very large surface overall and which are in direct contact with the ozone gas, in the arising gas bubble comprising ozone. The contact of the ozone with water and/or with hydrogen peroxide results in the activation of the liquids by a reaction between water and/or hydrogen peroxide and the ozone. This reaction results in the splitting of the water or the hydrogen peroxide and to radical formation. The hydroxide radicals $OH^-$ are reactive and aggressive and effect the desired sterilization success by killing microorganisms.

Due to the comparatively large contact surface between the liquid with the ozone gas, a number of the named reactions are stimulated so that a correspondingly high yield of $OH^-$ radicals is present.

Provision is made in a further embodiment of the invention that the introduction of a sterilization agent into the sterilization chamber takes place at a pressure in the sterilization chamber which is below the atmospheric pressure.

This procedure makes it possible always to keep the aerosol container and/or aerosol generator at a pressure value which is below the atmospheric pressure during the entire operation. This procedure brings along the advantage that a topping up of the aerosol container with hydrogen peroxide or water is particularly simple since only one metering valve has to be opened through which the corresponding liquid can then subsequently be drawn.

It is moreover conceivable that the holding of the support pressure preferably takes place for a duration, in accordance with the fifth step, that is, the holding of the support pressure for a point in time or a duration, whose length is in the range <20 minutes, preferably <10 minutes, and particularly preferably <5 minutes.

Provision can furthermore advantageously be made that the duration between two application steps taking place successively, preferably in accordance with the fourth step, that is, the application of the support pressure, is in the range <20 minutes, preferably <15 minutes, and particularly preferably <10 minutes.

It is furthermore conceivable that after the last method step, in particular the seventh step, that is, the application of the at least one second support pressure, or after termination of the sterilization, the flushing and degassing of the sterilization chamber is carried out, wherein the flushing and degassing is preferably carried out several times.

It is conceivable to design this flushing and degassing phase by repetitions of evacuations and ventilations. It is likewise advantageously conceivable to provide a drying phase which is preferably carried out in the evacuated state of the sterilization chamber. The sterilization procedure can then be terminated.

An advantageous embodiment of the method can comprise the sequence of steps two to five lasting approximately 15 to 20 minutes, preferably approximately 18 minutes.

The invention furthermore relates to a sterilization apparatus having the features of claim 18. Provision is accordingly made that the sterilization apparatus has at least one sterilization chamber for the reception of at least one object to be sterilized, at least one first means for the supply and/or removal of a sterilization agent, and at least one second means by means of which at least one first support pressure and at least one second support pressure can be applied, and wherein at the first support pressure of the sterilization agent a sterilization of a first region of the object can be carried out and a sterilization of a second region of the object can be carried out at the second support pressure.

The first means can advantageously be a supply line in which at least one cut-off valve is present. It is conceivable that the supply line is simultaneously a removal line. It is, however, generally advantageously possible to make the supply line and the removal line separately from one another. The second means can have a support gas supply with a corresponding pressure regulation, wherein the supply line for the support gas advantageously has at least one valve. Different support pressures can be set via the pressure regulation.

Provision can be made that the sterilization apparatus has at least one control and/or regulation means by means of which the sterilization procedure can be controlled and/or regulated and/or monitored, can preferably be semiautomatically and/or fully automatically controlled and/or regulated and/or monitored. This control and/or regulation means can, for example, be a part of the central control and/or regulation unit of the sterilization apparatus.

It is further possible that the first support pressure and/or the second support pressure can be applied by means of the second means at a pressure which is particularly advantageously below atmospheric pressure. It is alternatively also conceivable that the first support pressure and/or the second support pressure can be applied by means of the second means at a pressure which is at or above atmospheric pressure.

It is particularly advantageous if a method in accordance with one of the claims 1 to 17 can be carried out with the sterilization apparatus. It is conceivable that the carrying out of the method can be controlled and/or regulated and/or monitored, can preferably be semiautomatically and/or fully automatically controlled and/or regulated and/or monitored, by the control and/or regulation means.

The present invention furthermore relates to a use of a method for sterilizing and/or of a sterilization apparatus having the features of claim 21. Provision is accordingly made that a method in accordance with claims 1 to 17 and/or a sterilization apparatus in accordance with one of the claims 18 to 20 is used for sterilizing at least one object, in particular a medical hose kit.

The present invention further relates to a sterilized object having the features of claim 22. Provision is accordingly made that a sterilized object, in particular a medical hose kit, is obtained using a sterilization apparatus in accordance with one of the claims 18 to 20 and/or by means of a method in accordance with one of the claims 1 to 17.

The object preferably has at least one means by means of which the sterilization procedure which has taken place is or can be displayed. This can, for example, be a print which indicates the type of the sterilization method and is e.g. applied to the packaging of the hose kit. It is particularly advantageous if the means or the print is made such that its quality is changed by the sterilization procedure and hereby allows the recognition that the sterilization procedure was successful. This can take place, for example, by a color change of the means as a consequence of the contact with the sterilization agent. It is conceivable that the means indicates or that it can be indicated by the means whether the method in accordance with one of the claims 1 to 17 was carried out successfully or not.

Figure 2:
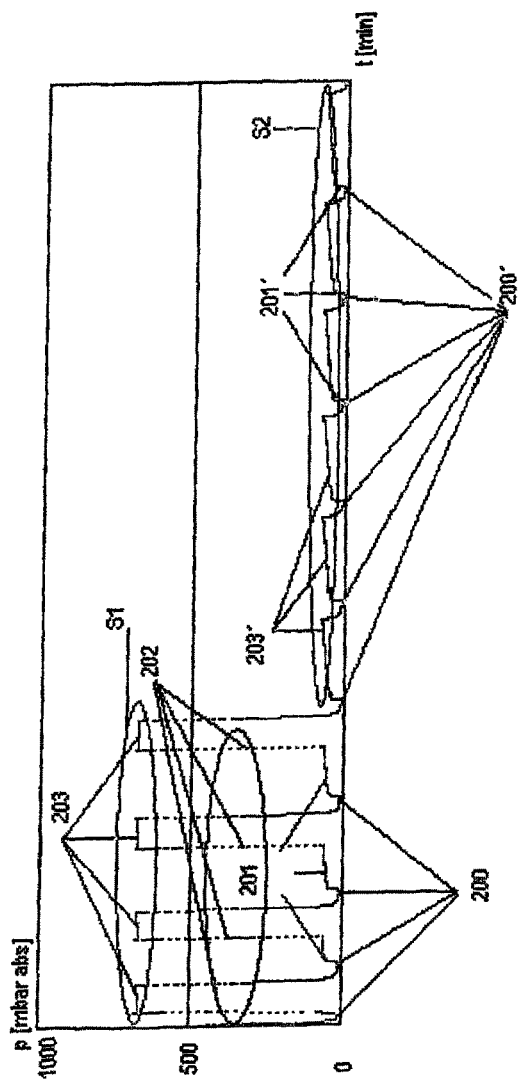
Figure 3:
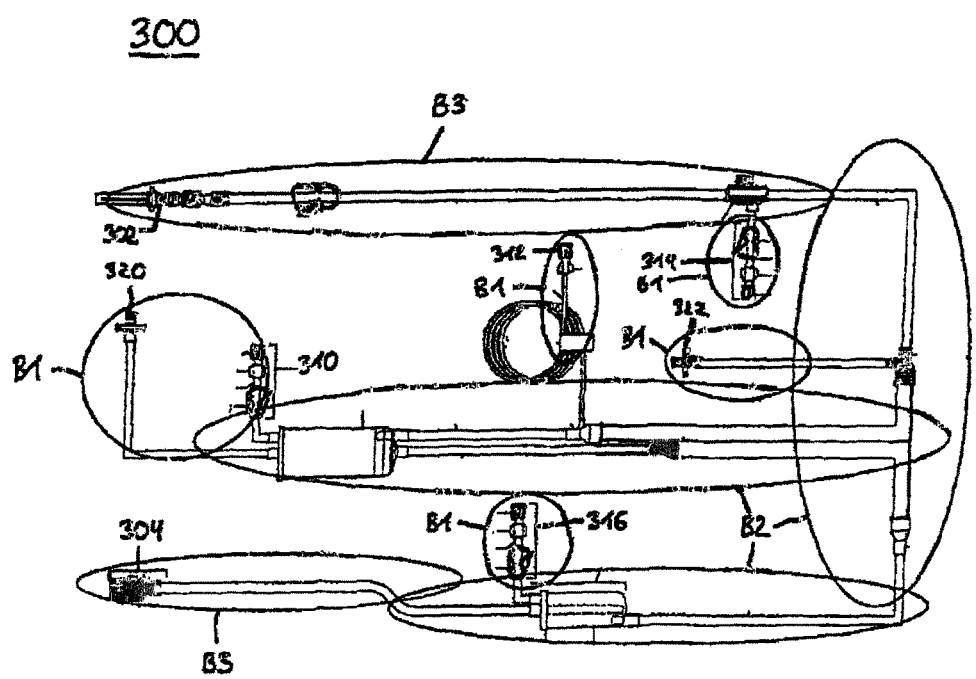

Further details and advantages will now be explained in more detail with reference to an embodiment shown in the drawing. There are shown:

FIG. 1: a schematic representation of a sterilization apparatus in accordance with the present invention;

FIG. 2: a representation of the pressure profile in the sterilization chamber during a sterilization cycle; and FIG. 3: a schematic representation of a medical hose kit with indication of the different sterilization regions.

FIG. 1 shows a block diagram for an embodiment of a sterilization apparatus in accordance with the present invention. A sterilization chamber is labeled by the reference numeral 10 which can, for example, have a volume of at least 1 m³ and a door which serves both loading and unloading. The objects to be sterilized can be introduced into the sterilization chamber 10, for example, on steel baskets on one or more levels. 150 to 200 products can be sterilized simultaneously depending on the product size. An aerospace container 20 or a vaporizer 20 is connected before the sterilization chamber 10.

As can furthermore be seen from FIG. 1, an oxygen generator 40 is connected before the ozone generator 30 and 95% oxygen can be acquired from the environmental air in it. A molecular screen or zeolite serves this purpose, for example. The oxygen is converted into ozone in the ozone generator 30, which can take place, for example, by a dielectric barrier discharge.

If the method in accordance with the invention is only carried out with hydrogen peroxide, the Figure shown in FIG. 1 can be made correspondingly modified. For example, the ozone generator 30 can then be dispensed with. Instead, for example, a reservoir or tank can be provided for the hydrogen peroxide or generally a hydrogen peroxide supply can be provided. The hydrogen peroxide is preferably introduced into the sterilization chamber 10 in steam form, for instance as liquid vaporized by evacuation.

A catalytic converter is labeled by the reference numeral 100 in FIG. 1 which is suitable to decompose the sterilization agent after its use, in particular to decompose hydrogen peroxide and/or ozone or their reaction products. Only water and oxygen are then created as decomposition products. The catalyst 100 can, for example, be manganese dioxide.

To generate the desired vacuum in the sterilization chamber 10, a vacuum pump 50 is connected after said sterilization chamber which results in an evacuation of the sterilization chamber 10 with an opened valve V6 and with a vacuum pump 50 in operation. Sterile air is introduced as the support gas into the sterilization chamber 10 via the valve V7. Finally, a unit is indicated by the reference numeral 110 which serves the metering in of water and/or hydrogen peroxide into the aerosol container 20 or to the vaporizer 20.

The sterilization procedure has the following form in detail:

After the insertion of the object or objects into the sterilization chamber 10, a vacuum is generated in the sterilization chamber 10, for which purpose only the valve V6 in accordance with FIG. 1 is opened and all the further valves V1, V2, V3, V4, possibly V5, V7 and V8, are closed. The generation of the vacuum results in a reduction of the chamber pressure.

The pressure in the chamber 10 preferably drops to a value <10 mbar in step 200 due to the evacuation of the sterilization chamber 10 by means of the vacuum pump 200.

For the humidification, the valve V5 in the line between the aerosol container 20 or the vaporizer 20 and the sterilization chamber 10 can e.g. be opened so that a vaporization of the liquid in the aerosol container 20 takes place, provided its vapor pressure is fallen below. If the vapor pressure of the liquid, i.e. for example of the mixture of water and hydrogen peroxide, is fallen below in the aerosol container, it starts to vaporize and in this manner enters into the sterilization chamber 10. The vacuum pump 50 is thus not used only for evacuating, but also for vaporizing the liquid in the aerosol container 20.

A sterilization agent is actively introduced into the sterilization chamber 10 simultaneously with the step of humidifying. This method step is labeled by the reference numeral 201 in FIG. 2. Hydrogen peroxide is advantageously introduced as the sterilization agent into the sterilization chamber as vapor here, for example.

Alternatively, the creation of hydroxide radicals can take place due to the contact of the ozone with water and/or hydrogen peroxide, said hydroxide radicals entering into the sterilization chamber 10 with the aerosol and there contributing to the sterilization process or representing the decisive sterilization agent.

The valves V3 and V5 or V4 and V5 are opened and all the further valves are closed during the method step 201 in accordance with FIG. 3. The aerosol containing ozone enters into the sterilization chamber 10 due to the pressure drop between the ozone generator 30 and the sterilization chamber 10.

This applies correspondingly to the hydrogen peroxide vapor when hydrogen peroxide is used as the sterilization agent instead of ozone.

A pressure increase thereby occurs such as can be seen from FIG. 2. This pressure increase is a measure for the quantity of the sterilization agent in the sterilization chamber 10. In this respect, the concentration is set to a value ideal for the product to be sterilized.

After the introduction of the sterilization agent, the pressure in the sterilization chamber 10 is increased by means of a support gas via the valve V7, as is shown in step 202 in accordance with FIG. 2. In the embodiment shown there, the pressure is increased to a first support pressure of approximately 500 mbar abs. This support gas enters into the sterilization chamber 10 in that the valve 7 in accordance with FIG. 1 is opened for a predetermined duration or until a specific pressure value is reached. All the further valves of the apparatus are closed during this method step. V5 can alternatively also be open.

The sterilization phase in which the first pressure gas is applied is called the first sterilization phase S1.

As can further be seen from FIG. 2, the first support pressure is held in the sterilization chamber 10 for a specific duration. This method step is identified by the reference numeral 203 in FIG. 2 and can be, for example, a minute or in the minute region.

After the holding of the support pressure for a specific duration in accordance with step 203 in FIG. 2, this process step comprising the steps 200 to 203 are carried out four times in total, i.e. it is evacuated, then humidified and the sterilization agent is introduced and then the first support pressure is again generated and held for a specific duration.

After the fourfold carrying out of the steps 200 to 203, the first sterilization phase S1 is terminated and the process continues with the second sterilization phase S2. In the sterilization phase S2, the second support pressure is applied which here amounts to 50 mbar abs and the steps 200', 201', 202' and 203' are carried out a total of six times. In this respect, steps 200' to 203' correspond to steps 200 to 203 from the sterilization phase S1, i.e. it is evacuated, then humidified and the sterilization agent is introduced and then the second support pressure is generated again, with the difference that the second support pressure in the sterilization phase S2 amounts to 50 mbar abs.

Due to the fact that the filling of the sterilization chamber 10 with sterilizing agent in accordance with step 201, 201', 201" is terminated when a substantial underpressure is present in the sterilization chamber 10, it can generally be achieved that an underpressure is always present in the aerosol generator 20. This makes it possible that liquid, i.e. water, hydrogen peroxide and/or a mixture of both substances, can subsequently easily be drawn from a reservoir 110 by opening the valve V4.

As can furthermore be seen from FIG. 1, the pump 50 is in communication at the outlet side with the catalyst 100 so that the medium arising at the pressure side of the pump can be decomposed in the catalyst 100.

It is generally conceivable to repeat and/or to vary the sterilization phases S1 and S2, for example, or to carry out further sterilization phases at different support pressures subsequently to the sterilization phases shown in FIG. 2.

This is followed in the embodiment shown here by the flushing and degassing of the sterilization chamber 10 by multiple evacuation and ventilation. This phase is not shown in any more detail in FIG. 2.

An evacuation and a ventilation of the sterilization chamber 10 takes place multiple times during the flushing and degassing phase. This phase can be followed by a drying phase in which there is preferably a vacuum in the sterilization chamber 10.

FIG. 3 shows a hose system 300 or a so-called hose kit 300 which was sterilized by means of the apparatus and method shown in FIGS. 1 and 2. It is a hose kit 300 for dialysis which can have a total hose length of up to 6 m in dependence of the treatment process.

The packing for the hose kit 300 in which the hose kit 300 is, however, preferably sterilized is not shown. It is conceivable that at least one support pressure above the atmospheric pressure is applied or is being applied in such a case.

The hose kit 300 in accordance with FIG. 3 is a hose kit 300 for the extracorporeal blood circuit which in particular has a needle 302 for connection of the hose kit 300, e.g. to the shunt of the patient, a connector 304 e.g. for connection to the dialyzer, not shown, inflows and outflows 310, 312, 314, 316 closed by closure caps and pressure measurement connections 320, 322.

The regions labeled with B1 are sterilized by the application of the first support pressure of approximately 500 mbar abs, that is, during the sterilization phase S1 shown in more detail in FIG. 2. All the regions of the hose kit 300 in which the lumen of the hose kit 300 is closed at the end side are affected, that is, the inflows or outflows 310, 312, 314, 316 closed by closure caps and the pressure measurement connections 320, 322. It is conceivable that with particularly long hose kits 300, the middle region of the hose kit 300 is likewise sterilized during the sterilization phase S1.

The regions labeled by B2 are likewise sterilized by the application of the first support pressure of approximately 500 mbar abs. All the regions of the hose kit 300 which are in the inner region of the lumen of the hose kit 300 are affected so that the first support pressure 300 is necessary or sufficient to transport the sterilization agent in it.

The regions labeled with B3 are sterilized by the application of the second support pressure or gassing pressure of approximately 50 mbar abs, that is, during the sterilization phase S2 shown in more detail in FIG. 2. These regions in FIG. 3 are here the start regions and end regions of the hose kit 300, that is, the regions which follow the needle 302 and the connection 304 respectively.

The invention claimed is:

1. A method for sterilizing at least one object (300), wherein the object (300) is exposed to a sterilization agent, wherein at least one first support pressure and at least one second support pressure different from the first support pressure are applied and wherein a sterilization of at least one first region (B1) of the object (300) takes place by the sterilization agent at the first support pressure and a sterilization of at least one second region (B2) of the object (300) takes place at the second support pressure, characterized in that the at least one first support pressure and the at least one second support pressure are generated by introducing a support gas into a sterilization chamber (10) after introduction of the sterilization agent.

2. A method in accordance with claim 1, characterized in that the sterilization agent at least partly includes ozone and/or hydrogen peroxide or one or more of the reaction products of these substances.

3. A method in accordance with claim 1, characterized in that the support gas includes at least partially an inert gas and/or sterile air.

4. A method in accordance with claim 1, characterized in that in a first step, the object (300) to be sterilized is inserted into a sterilization chamber (10); in a second step (200), the sterilization chamber (10) is evacuated; in a third step (201), the sterilization chamber (10) is humidified and sterilization agent is introduced into the sterilization chamber (10); in a fourth step (202), the first support pressure is applied; in a fifth step (203), the first support pressure is maintained for a point in time or for a duration; in a sixth step, steps two to five are repeated once or a multiple of times; and in a seventh step, the at least one second support pressure is applied.

5. A method in accordance with claim 4, characterized in that in the seventh step, steps two to five or two to six are carried out at the second support pressure.

6. A method in accordance with claim 4, characterized in that in at least one further step, one or more further support pressures are applied; and in that steps two to five or two to six are accordingly carried out at the further support pressures.

7. A method in accordance with claim 4, characterized in that the humidification of the sterilization chamber (10) takes place in that a liquid, in particular a mixture containing water and hydrogen peroxide, is brought to vaporization by application of a vacuum, in particular by the evacuation, and the vaporized liquid is supplied to the sterilization chamber (10).

8. A method in accordance with claim 1, characterized in that the first support pressure is at least approximately 500 mbar abs and/or the second support pressure is at least approximately 50 mbar abs.

9. A method in accordance with claim 1, characterized in that a third support pressure is applied, wherein the third support pressure is preferably up to approximately 50 mbar abs and/or corresponds to the gassing pressure without additional introduction of a support gas.

10. A method in accordance with claim 1, characterized in that the sterilization agent is introduced into the sterilization chamber (10) in the form of an aerosol.

11. A method in accordance with claim 10, characterized in that the aerosol is formed by vapor containing hydrogen peroxide; and/or in that the aerosol is created by introduction of ozone into a liquid which contains water and/or hydrogen peroxide.

12. A method in accordance with claim 1, characterized in that the introduction of a sterilization agent into the sterilization chamber (10) takes place at a pressure in the sterilization chamber (10) which is below the atmospheric pressure.

13. A method in accordance with claim 1, characterized in that the holding of the first support pressure takes place for a duration whose length is in the range <20 minutes.

14. A method in accordance with claim 1, characterized in that the duration between the first and second application steps taking place successively is in the range <20 minutes.

15. A method in accordance with claim 4, characterized in that, after the seventh step, or after termination of the sterilization, the flushing and degassing of the sterilization chamber (10) is carried out, with the flushing and degassing preferably being carried out a multiple of times.

16. A method in accordance with claim 4, characterized in that the sequence of the steps two to five lasts approximately 15 to 20 minutes.

17. The method in accordance with claim 1, wherein the at least one object (300) is a medical hose kit (300).

18. A method in accordance with claim 1, characterized in that the holding of the first support pressure takes place for a duration whose length is in the range <10 minutes.

19. A method in accordance with claim 1, characterized in that the holding of the first support pressure takes place for a duration whose length is in the range <5 minutes.

20. A method in accordance with claim 1, characterized in that the duration between the first and second application steps taking place successively is in the range <15 minutes.

21. A method in accordance with claim 1, characterized in that the duration between the first and second application steps taking place successively is in the range <10 minutes.

22. A method in accordance with claim 4, characterized in that the sequence of the steps two to five lasts approximately 18 minutes.

* * * * *